US010242855B1

(12) United States Patent
Lewis

(10) Patent No.: US 10,242,855 B1
(45) Date of Patent: Mar. 26, 2019

(54) DETECTOR, SYSTEM AND METHOD FOR DROPLET AND/OR CLUSTER BEAM SPECTROSCOPY

(71) Applicant: The United States of America, as represented by the Secretary of the Air Force, Washington, DC (US)

(72) Inventor: William K Lewis, Dayton, OH (US)

(73) Assignee: The United States of America as requested by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/654,147

(22) Filed: Jul. 19, 2017

Related U.S. Application Data

(60) Provisional application No. 62/397,433, filed on Sep. 21, 2016.

(51) Int. Cl.
  *H01J 49/02* (2006.01)
  *H01J 49/00* (2006.01)
  *H01J 49/14* (2006.01)
  *H01J 49/04* (2006.01)

(52) U.S. Cl.
  CPC ........ *H01J 49/025* (2013.01); *H01J 49/0031* (2013.01); *H01J 49/0445* (2013.01); *H01J 49/147* (2013.01)

(58) Field of Classification Search
  CPC .. H01J 49/025; H01J 49/0027; H01J 49/0031; H01J 49/0445; H01J 49/147; G01L 21/32
  See application file for complete search history.

(56) References Cited

U.S. PATENT DOCUMENTS

| 4,792,763 | A | * | 12/1988 | Haas | G01L 21/32 313/632 |
| 5,250,906 | A | * | 10/1993 | Bills | H01J 41/04 250/374 |
| 5,296,817 | A | * | 3/1994 | Bills | H01J 41/04 250/374 |
| 2011/0054686 | A1 | * | 3/2011 | Lee | G05D 1/027 700/253 |
| 2011/0163754 | A1 | * | 7/2011 | Carmichael | G01L 21/32 324/460 |

OTHER PUBLICATIONS

Choi et al, "Infrared Spectroscopy of Helium Nanodroplets: Novel Methods for Physics and Chemistry", International Reviews in Physical Chemistry, vol. 25, Nos. 1-2, Jan.-Jun. 2006, 15-25.*

(Continued)

*Primary Examiner* — David E Smith
(74) *Attorney, Agent, or Firm* — AFMCLO/JAZ; James F McBride

(57) ABSTRACT

A beam ionization gauge (BIG) detector is disclosed for use in spectroscopy and configured to receive an analyte beam along a beam path. The BIG detector includes a filament configured to emit electrons and a grid. The grid is positioned substantially adjacent to the filament and configured to produce ions by directing the electrons to collide with the analyte beam along the beam path. A collector is positioned substantially adjacent to the grid to define the beam path therebetween and configured to detect the ions produced by the collisions of electrons with the analyte beam.

18 Claims, 8 Drawing Sheets

(56) References Cited

OTHER PUBLICATIONS

Choi et al., "Infrared Spectroscopy of Helium Nanodroplets: Novel Methods for Physics and Chemistry", Jan.-Jun. 2006, International Reviews in Physical Chemistry, vol. 25, Nos. 1-2 (pp. 15-75).
Jordan Tof Products, Inc., "Instruction Manual for FIG—Fast Ion Gage Power Supply D-403 Rev-2", <www.rmjordan.com/manuals/D403man.pdf> (11 Pages).
Thomas et al "Note: A simple detection method for helium droplet spectroscopy experiments" Dec. 2016, vol. 3, No. 8, AIP Review of Scientific Instruments <aip.scitation.org/doi/abs/10.1063/1.4973775?journalCode=rsi&> (5 Pages).

* cited by examiner

DETECTOR, SYSTEM AND METHOD FOR DROPLET AND/OR CLUSTER BEAM SPECTROSCOPY

CROSS REFERENCE TO RELATED APPLICATIONS

This application claims the benefit under 35 U.S.C. § 119(e) of U.S. Provisional Patent Application Ser. No. 62/397,433 filed on Sep. 21, 2016, the entire contents of which are incorporated herein by reference.

GOVERNMENT INTEREST

The invention described herein may be manufactured and used by or for the Government of the United States for all governmental purposes without the payment of any royalty.

FIELD OF THE INVENTION

The present invention relates to systems and methods for mass spectrometry analysis, and more particularly to droplet and/or cluster beam detection in spectroscopy systems and methods.

BACKGROUND OF THE INVENTION

Helium droplet spectroscopy is currently established as one of the leading experimental techniques for the production and study of novel clusters and complexes. The success of the approach is largely due to two factors: the remarkable versatility of the approach as an assembly technique to produce novel species, and the method's facilitation of spectroscopic interrogation of the species produced. The low droplet temperature (e.g., 0.37 K) and high mobility of dopants inside the droplet result in efficient coagulation of captured impurities into clusters and complexes. Because the helium "solvent" interacts so weakly with dopants placed in the droplets, coagulation (rather than solvent-separation) of the dopants occurs quickly for virtually any combination of atoms and molecules chosen. Many species formed in helium droplets would be either difficult or impossible to form by other methods.

The success of the helium droplet spectroscopy approach is not solely due to versatility. Its success can also be attributed to the method's ability to facilitate the spectroscopic interrogation of different species. Spectroscopic measurements, ranging from the microwave to the ultraviolet, are possible because the helium droplet itself is transparent to photons with energies less than 20 eV. Additionally, the low temperature in the droplet tends to greatly simplify the spectra obtained. As mentioned above, the interaction between the assembled species and the surrounding helium is extremely weak. Consequently, the perturbations to the species are typically minimal, and the gas phase Hamiltonian continues to be applicable. Notably, the superfluid nature of the helium solvent permits the rotation of the solvated structure (albeit with modified rotational constants), thus preserving the rotational fine structure in the spectra.

In contrast to the aforementioned advantages, one significant disadvantage to potential practitioners of helium droplet spectrometry is the costs associated with the equipment required to setup the experiments. More specifically, the laser system used to excite transitions in the species under study, and also the detector necessary to monitor the photon-induced depletion of the droplet beam, can be expensive to implement. Recent advances in laser technology such as the increased availability and performance of quantum cascade lasers (QCLs), for example, are creating more cost-effective options for laser sources. In regards to beam detection, most users utilize either a bolometer or a quadrupole mass spectrometer (QMS). The bolometer is the less expensive and more sensitive of the two options, but it still uses a liquid helium cryostat to ensure sufficiently sensitive detection. While the QMS does not require a liquid helium supply, it is typically more expensive to purchase.

The paper titled "Infrared spectroscopy of helium nanodroplets: novel methods for physics and chemistry" by M. Y. Choi et al. discusses the typical prior art arrangements of a helium droplet mass spectrometer arrangement 100 and helium droplet bolometer arrangement 200 as illustrated respectively in FIGS. 1 and 2 infra. Referring to FIG. 1, the schematic diagram shows the helium droplet mass spectrometer arrangement 100 including a helium droplet source chamber 110, pick-up cell chamber 120 and an off-axis mass spectrometer 130 that receives an infrared laser light 140 directed at the droplet beam 111 along the droplet beam path 121. FIG. 2 shows helium droplet bolometer arrangement 200 including a helium droplet source chamber 210, pick-up cell chamber 220, laser multipass chamber 230 and a bolometer chamber 240. The laser multipass chamber 230 is used to cross the droplet beam 211 with multiple laser 250 passes.

Known techniques accomplish intentional doping of the droplets with the species of interest using a 'pick-up' technique which involves passing the beam 111/211 through the pick-up cell chamber 120/220, that is maintained at a pressure sufficient to permit the capture of the desired number of gas-phase atoms or molecules. The pick-up cells, shown schematically in FIGS. 1 and 2 as being within the pick-up cell chamber 120/220, may take on many different forms depending upon the dopant molecules or atoms of interest. Due to the optical transparency of the droplets, a wide range of possibilities for the cells exist, including simple gas cells and high-temperature ovens designed to evaporate highly refractive materials.

The infrared spectrum of a solvated molecule can therefore be obtained by recording the frequency dependence of the laser-induced attenuation of the helium beam. As shown in FIGS. 1 and 2, this recording may be accomplished using either a mass spectrometer 130 or bolometer chamber 240 to measure the helium beam flux, as would be appreciated by those skilled in the art.

Given the cost and complexity of current detectors, there exists an unmet need in the art for an effective, yet relatively inexpensive, droplet beam detector for use in such spectroscopy systems and methods.

This background information is provided to reveal information believed by the applicant to be of possible relevance to the present invention. No admission is necessarily intended, nor should be construed, that any of the preceding description constitutes prior art against the present invention.

BRIEF SUMMARY OF THE INVENTION

With the above in mind, embodiments of the present invention are related to a beam ionization gauge (BIG) detector for use in spectroscopy and configured to receive an analyte beam along a beam path. The BIG detector may include a filament configured to emit electrons, and a grid positioned substantially adjacent to the filament and configured to direct the electrons to collide with the analyte beam along the beam path to produce ions. A collector may be positioned substantially adjacent to the grid to define the beam path therebetween and may be configured to detect the ions when the electrons collide with the analyte beam along the beam path.

In various embodiments, the grid may be positioned substantially parallel with the collector. Also, the filament may be substantially aligned with the beam path.

In certain embodiments, a vacuum chamber may enclose the grid, collector and filament and may be configured to receive the analyte beam. As such, the vacuum chamber may include a window configured to receive light from a source (e.g., a laser beam) to be counter-propagated with the analyte beam.

In certain embodiments, the analyte beam may include a solvent and a dopant. Such a solvent may include droplets and/or clusters, such as helium droplets.

In various embodiments, an ion gauge controller may be coupled to the filament and the grid.

Embodiments may also be directed to a method of detection in spectroscopy using a beam ionization gauge (BIG) detector that includes a grid, a collector, and a filament, wherein the grid may be positioned adjacent to the collector to define a beam path therebetween, and wherein the filament may be positioned adjacent the grid, with the grid positioned between the filament and the beam path. The method may include receiving an analyte beam along the beam path, emitting electrons using the filament, using the grid to direct the electrons to collide with the analyte beam along the beam path to produce ions, and using the collector to detect the ions.

In various embodiments, the grid may be positioned substantially parallel with the collector and/or the filament may be substantially aligned with the beam path.

In certain embodiments, the method may include enclosing the grid, collector and filament in a vacuum chamber that may receive the analyte beam and/or counter-propagating light with the analyte beam via a window in the vacuum chamber.

The method may further include controlling the filament and the grid with an ion gauge controller.

Embodiments are also directed to a spectroscopy system that may include a beam source configured to produce a solvent beam, a pickup region configured to receive the solvent beam and add dopants thereto to define an analyte beam, and a beam ionization gauge (BIG) detector configured to receive the analyte beam along a beam path. The BIG detector may include a vacuum chamber enclosing a filament configured to emit electrons, a grid positioned substantially adjacent to the filament and configured to produce ions by directing the electrons to collide with the analyte beam along the beam path, and a collector positioned substantially adjacent to the grid to define the beam path therebetween and configured to detect the ions produced by the collision of electrons with the analyte beam. An ion gauge controller may be coupled to the filament and the grid. A source may be configured to generate light to interact with the analyte beam. Also, an analyzer may be configured to receive an output from the collector.

In certain embodiments, the grid may be positioned substantially parallel with the collector, and/or the filament may be aligned with the beam path. The beam source may be configured to produce the solvent beam including at least one of droplets and clusters, for example, helium clusters. Furthermore, the vacuum chamber may include a window, and the source may be a laser configured to generate a laser beam that is counter-propagated with the analyte beam through the window.

A purpose of the present embodiments, including the beam ionization gauge (BIG) detector, is to detect a droplet beam (e.g., a helium droplet beam or other cluster or droplet beam) and the depletion thereof during a spectroscopy test, experiment, or evaluation. As discussed above, helium droplet beam approaches are currently established as a preferred scientific technique for the production and spectroscopic study of atomic/molecular clusters and complexes.

Detection of the photo-induced depletion of a droplet beam during spectroscopy experiments requires a suitable detector. Existing options include a bolometer and a mass spectrometer, and both can be quite expensive. In the present embodiments, the BIG detector advantageously may provide a less costly option for detection than the existing technologies.

The present BIG detector may be configured to detect droplet (or cluster) beams with sufficient sensitivity, signal-to-noise, and time response to permit spectroscopy experiments to be performed on the species composing the beam, for example, with the use of a light source that may or may not be modulated. The geometry of the grid and collector (i.e. internal electrodes) may be designed to improve the sensitivity and signal-to-noise of beam detection (rather than background gas detection).

DETAILED DESCRIPTION OF THE INVENTION

Figure 1:
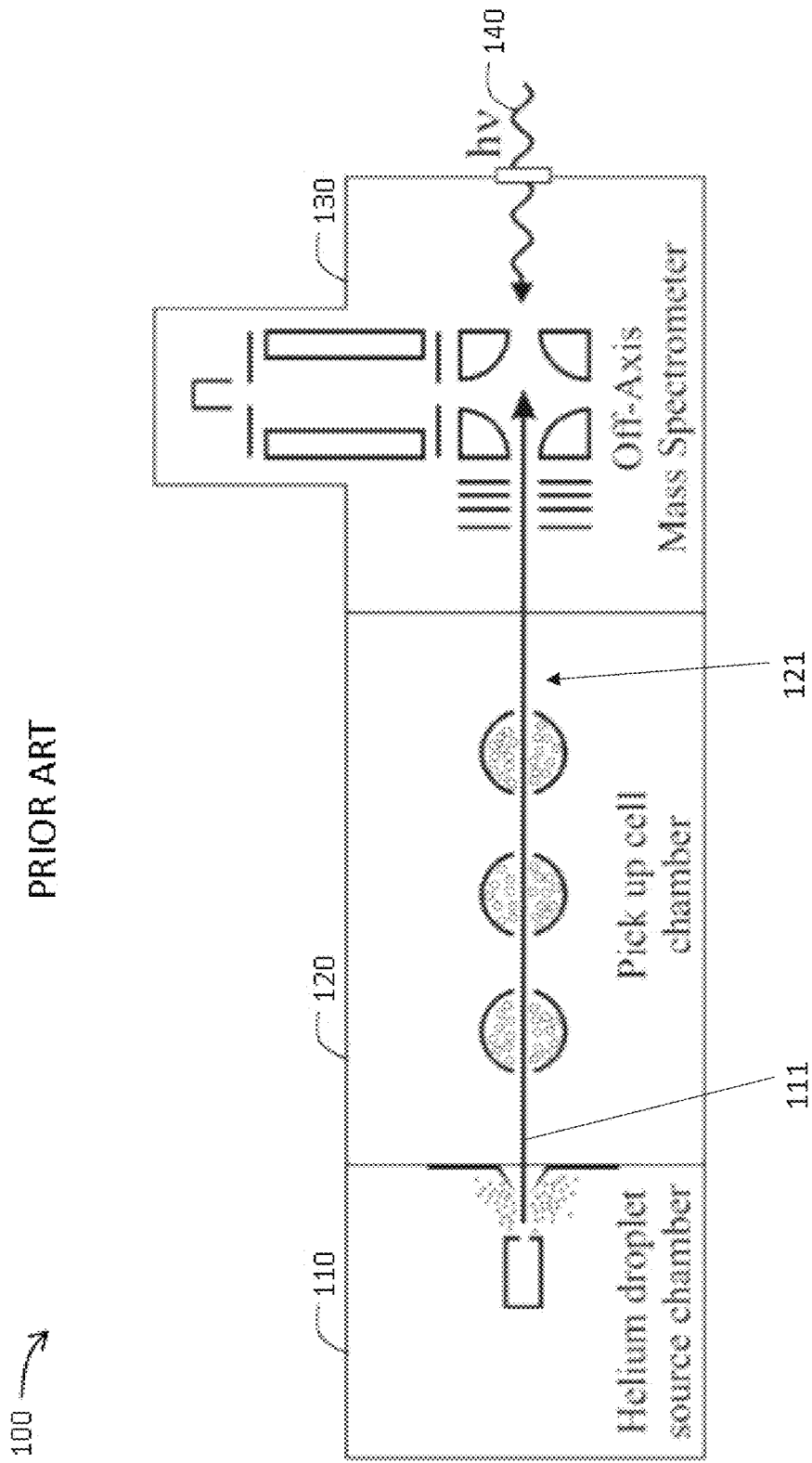
FIG. 1 is a schematic diagram of a typical helium droplet mass spectrometer arrangement according to the prior art.
Figure 2:
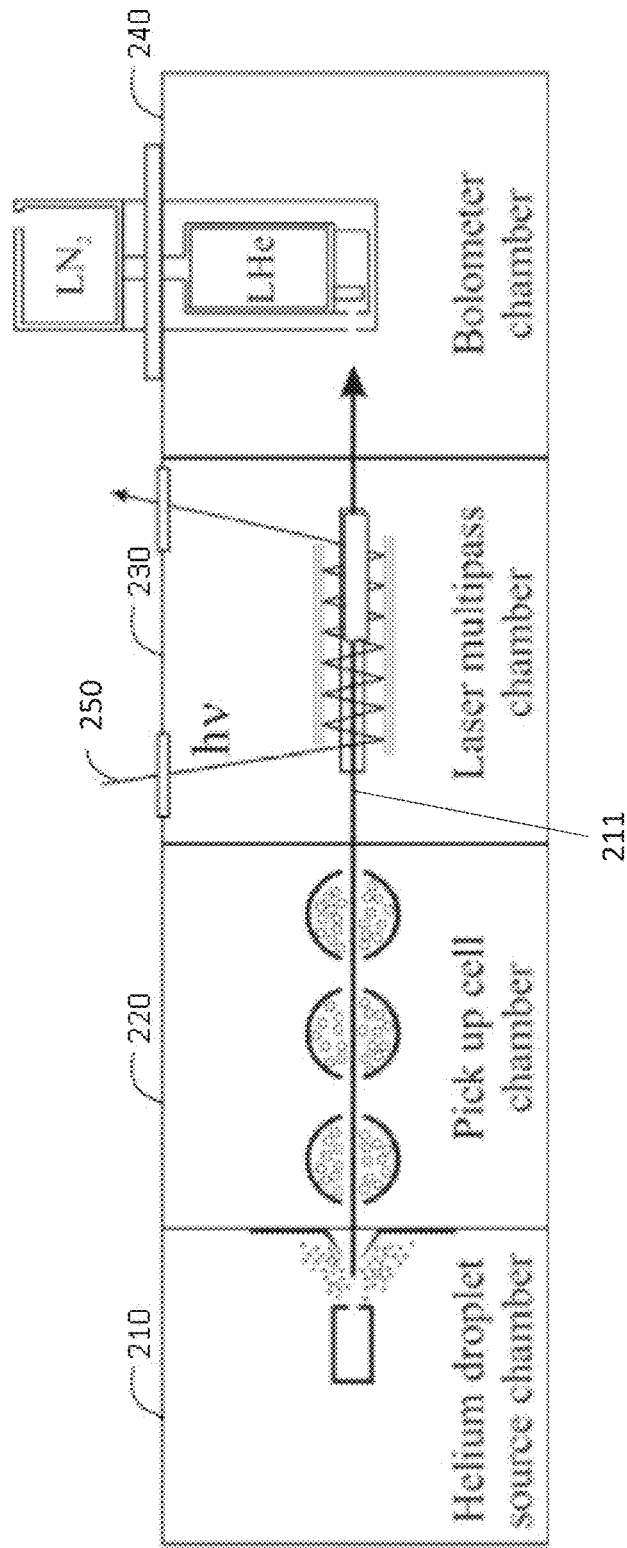
FIG. 2 is a schematic diagram of a typical helium droplet bolometer arrangement according to the prior art.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Referring to FIGS. 3-8, a beam ionization gauge (BIG) detector according to an embodiment of the present invention is now described in detail. Throughout this disclosure, the present invention may be referred to as a beam ionization gauge system, a BIG system, a detector system, a gauge, a detector, a device, a system, a product, and a method. Those skilled in the art will appreciate that this terminology is only illustrative and does not affect the scope of the invention.

A purpose of the present embodiments is to detect a droplet beam (e.g., a helium droplet beam or other cluster or droplet beam) and the depletion thereof during a spectroscopy experiment. As described above, helium droplet beam approaches are currently established as a preferred scientific technique for the production and spectroscopic study of atomic/molecular clusters and complexes.

The detection of the photo-induced depletion of a droplet beam during spectroscopy experiments requires a suitable detector. Existing options include a bolometer or a mass spectrometer, and both can be quite expensive. In the present embodiments, a beam ionization gauge (BIG) detector advantageously may provide a less costly yet sufficiently performing option for detection compared to these and other existing technologies.

The following description presents details regarding the development and evaluation of a less expensive droplet beam detector, which may be used in various applications such as in helium droplet spectroscopy experiments. The embodiments disclosed herein were developed, tested, and compared against the performance offered by a quadrupole mass spectrometer (QMS) arrangement, such as that described above. The results of these comparisons are explained more fully below.

Figure 3:
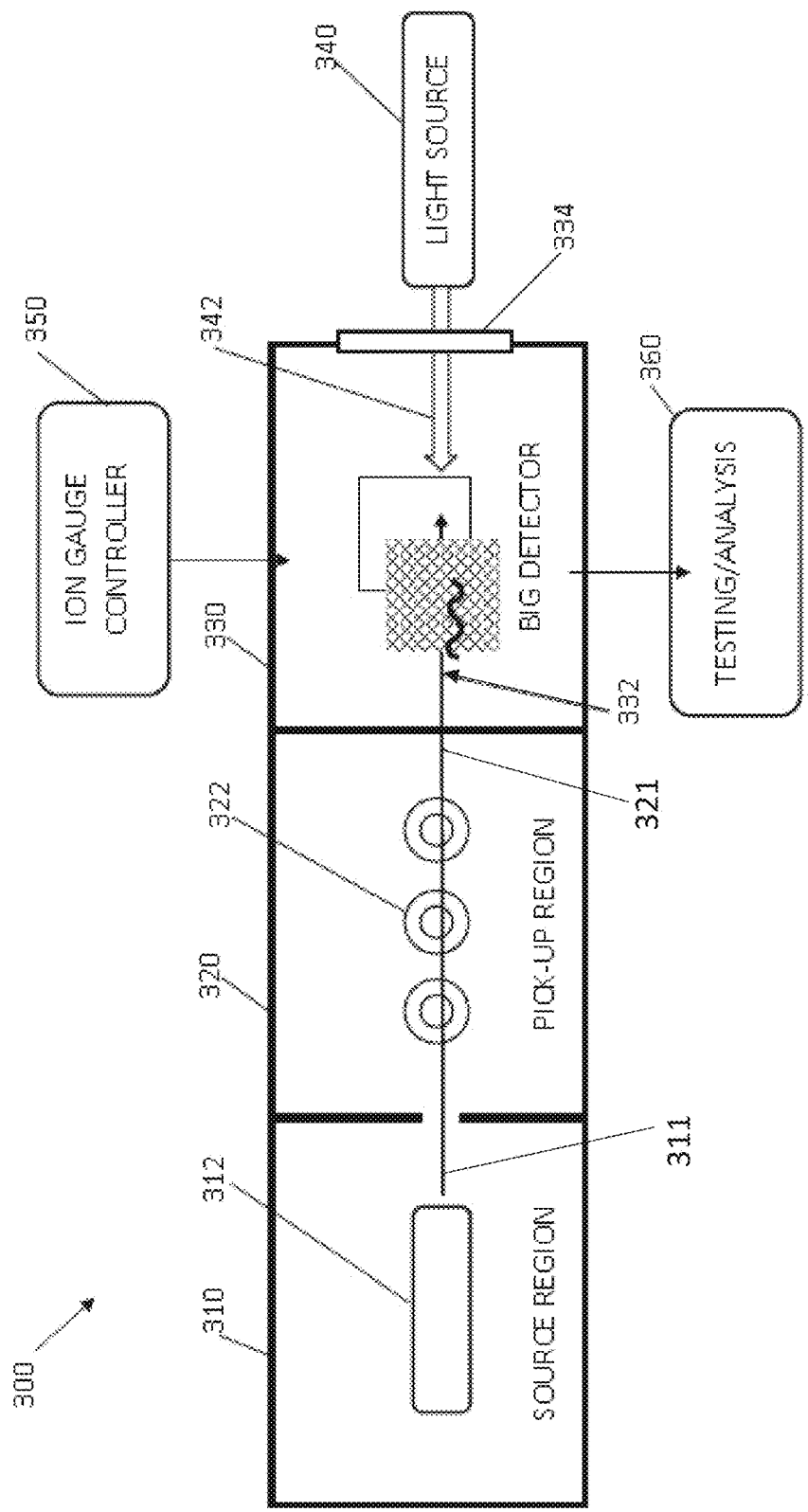
FIG. 3 is a schematic diagram of an exemplary mass spectrometer characterized by a beam ionization gauge detector according to an embodiment of the present invention.
Figure 4:
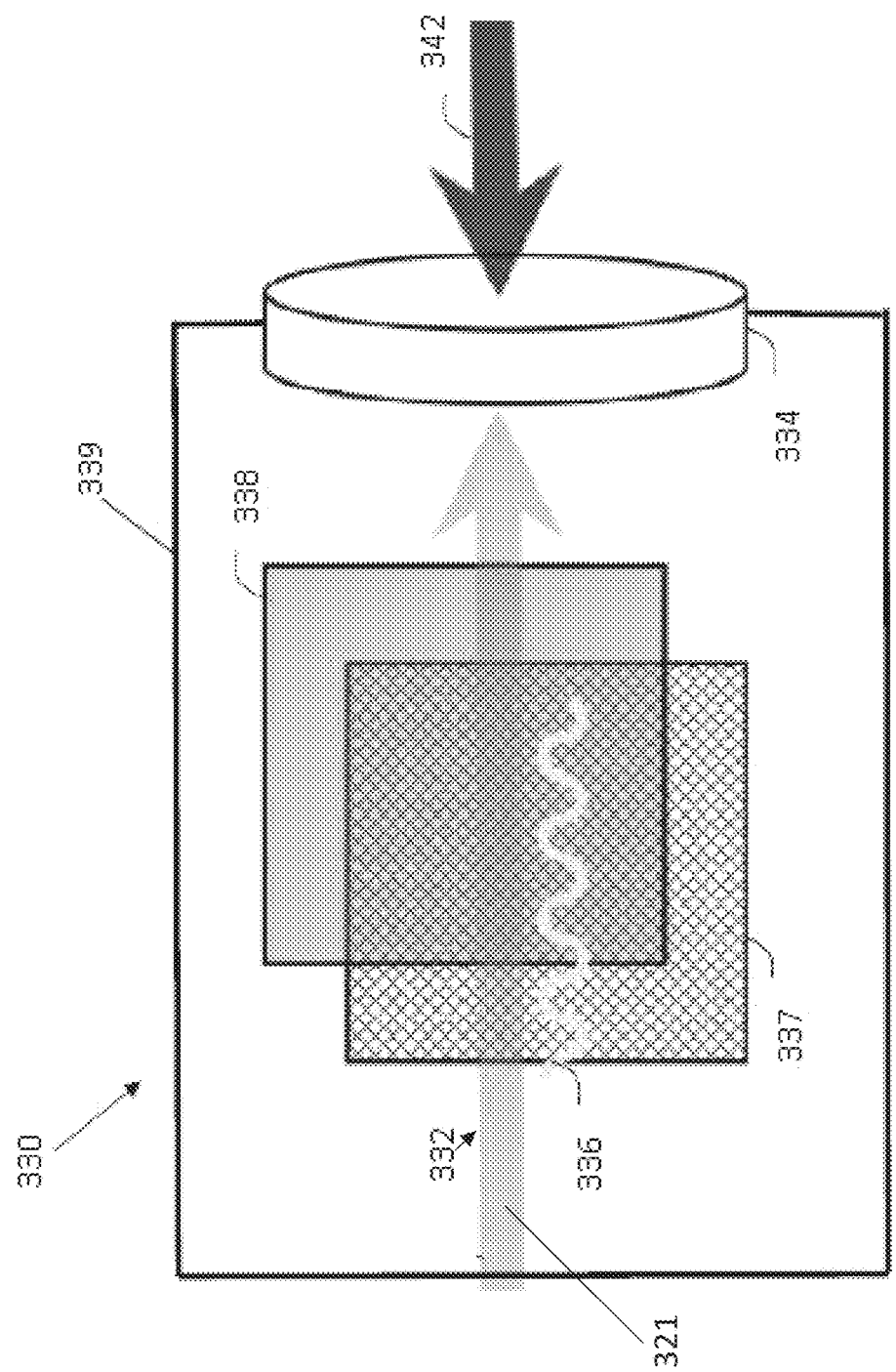
FIG. 4 is an enlarged representation view of the beam ionization gauge detector of FIG. 3.
Figure 5:
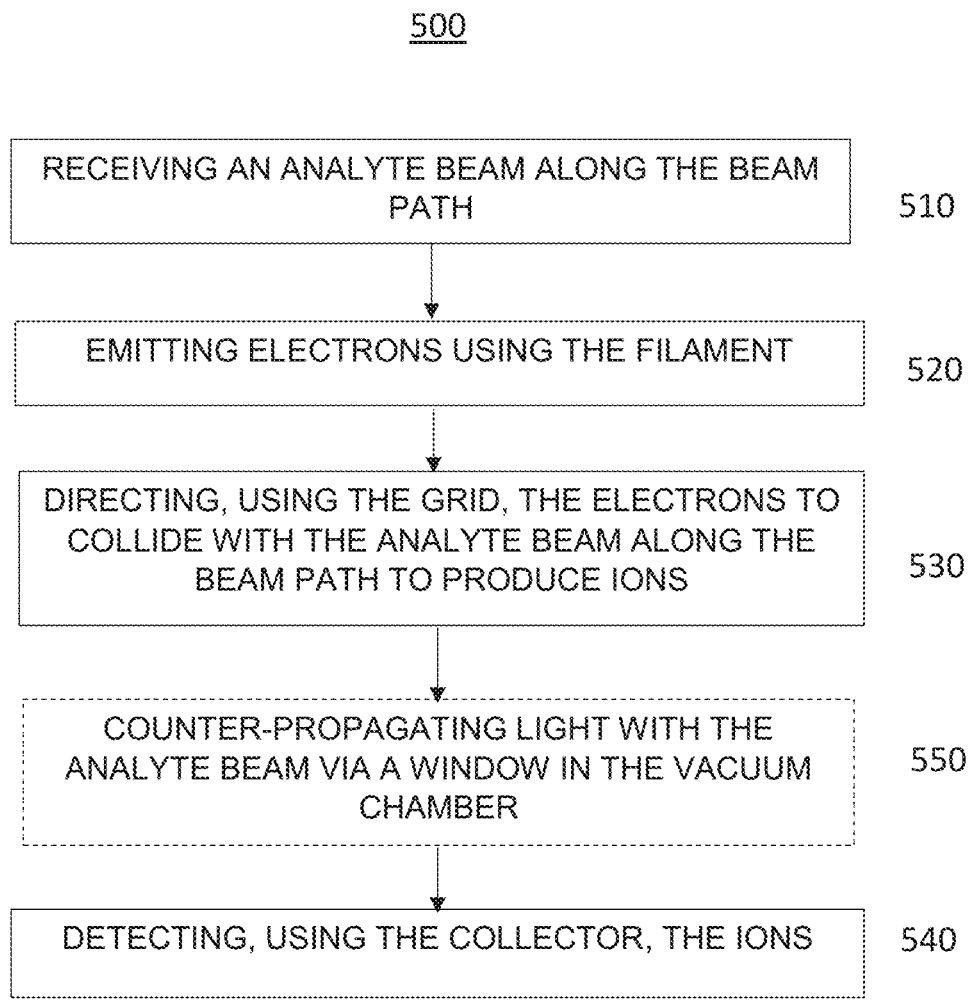
FIG. 5 is a flowchart illustrating various steps in a method of detection in spectroscopy using a beam ionization gauge detector according to an embodiment of the present invention.

A spectroscopy system 300 in accordance with features of the present invention will be described with reference to FIGS. 3 and 4. FIG. 3 is a schematic diagram of a spectroscopy system 300 including a beam ionization gauge (BIG) detector 330 according to an embodiment of the present invention. FIG. 4 is an enlarged representation view of the BIG detector 330 of FIG. 3.

A source region 310 (e.g., helium droplet source) may include a droplet or cluster source 312, a pick-up region 320 may include pickup cells 322, and the light source 340 (e.g., laser system) may operate as described in detail above with respect to the existing systems 100 and 200.

The source region 310 may define a beam source and may be configured to produce a solvent beam 311, for example, and without limitation, a helium droplet or cluster beam. The pickup region 320 may be configured to receive the solvent beam 311 and add dopants thereto to define an analyte beam 321. The BIG detector 330 may be configured to receive the analyte beam 321 along a beam path 332. The discussion herein may refer to helium droplets, but a person of skill in the art will immediately recognize that the principle of operation may work for any droplet or cluster that can be evaporated by an incident light.

In various embodiments, the BIG detector 330 may include a vacuum chamber 339 (e.g., a conFlat™ tee or CF vacuum chamber and flange) including a window 334 therein. In the exemplary embodiment, window 334 may be a calcium fluoride window.

The vacuum chamber 339 may enclose a filament 336 configured to emit electrons, a grid 337 positioned substantially adjacent to the filament 336 and configured to direct the electrons to collide with the analyte beam along the beam path 332 to produce ions, and a collector 338 positioned substantially adjacent to the grid 337 to define the beam path 332 therebetween and configured to detect the ions produced by the grid 337 directing electrons to collide with the analyte beam along the beam path 332. In the exemplary embodiment, the filament 336 is a tungsten emission filament, but any suitable filament for emitting electrons can be used.

In various embodiments, an ion gauge controller 350 may be coupled to the filament 336 and the grid 337 of the BIG detector 330. A light source 340 may be configured to generate light through a window 334, for example, and without limitation, to be counter-propagated with the analyte beam. The light source 340 may be a laser system (e.g., IR laser) or any light source capable of beam modulation, which can result from using spinning chopper wheels or built-in modulation functions as would be appreciated by those skilled in the art. To this end, any form of electromagnetic radiation that the analyte beam may absorb may be utilized in operation of the present invention, including, for example, and without limitation, ultraviolet, visible, near-infrared, infrared, gigahertz, or microwave light sources.

In the illustrated embodiment, light source 340 provides an IR laser beam 342 that is counter-propagated with the analyte beam to achieve the desired sensitivity. However, it will be appreciated that if the light source 340 is bright enough, the light may be crossed with, or otherwise interact with, the analyte beam in a perpendicular fashion and upstream of the BIG detector 330. As such, window 334 may not be present in some embodiments.

As part of system 300, an analyzer 360 or other testing device can be configured to receive an output from the collector 338. For example, and without limitation, the output of the collector 338 may be sent to an oscilloscope for initial testing or to a lock-in amplifier for spectroscopy experiments.

In various embodiments, the grid 337 may be positioned substantially parallel with the collector 338. Also, the filament 336 may be substantially aligned with the beam path 332.

Figure 6:
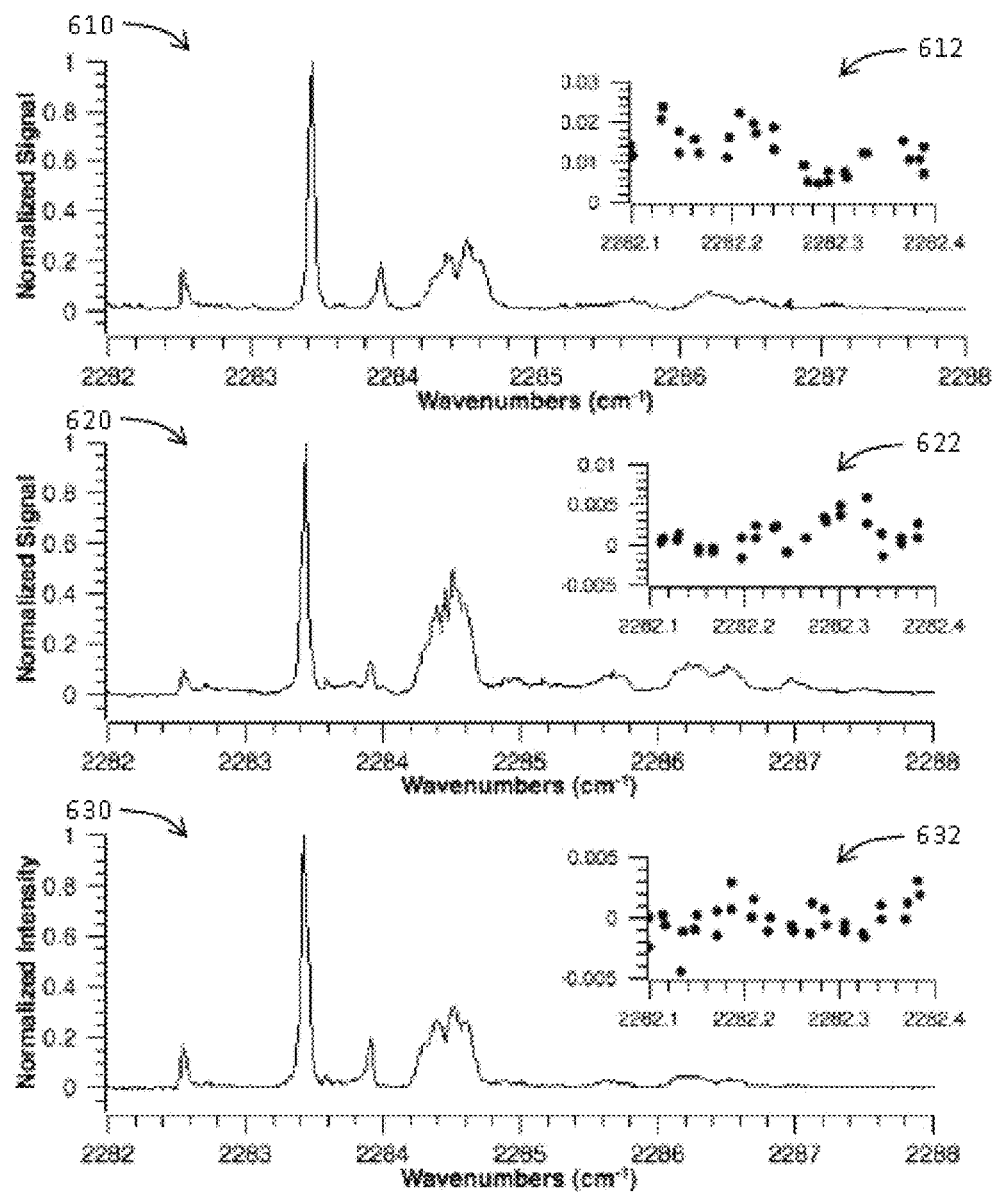
FIG. 6 illustrates comparative diagrams of exemplary infrared (IR) spectra collected using a beam ionization gauge detector according to an embodiment of the present invention, a quadrupole mass spectrometer (QMS) in high pass filter mode, and a QMS in mass selected mode, respectively.
Figure 7:
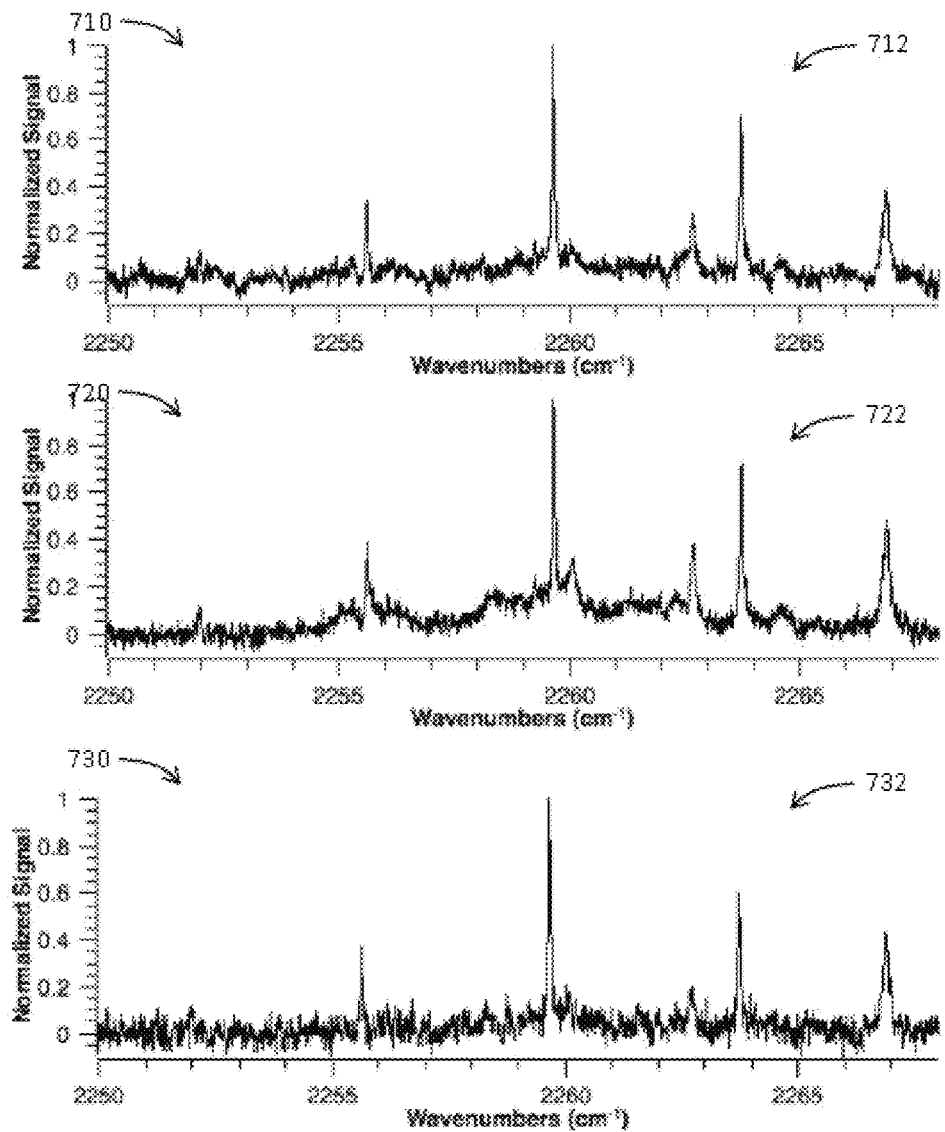
FIG. 7 illustrates comparative diagrams of exemplary infrared (IR) spectra collected using a beam ionization gauge detector according to an embodiment of the present invention, a QMS in high pass filter mode, and a QMS in mass selected mode, respectively.

Details of an exemplary implementation of a BIG detector 330 are now described with additional reference to actual data results from comparisons with existing QSM arrangements as depicted in FIGS. 6 and 7. The BIG detector 330 may include grid 337 (which may be made of wire mesh), a collector 338 (which may also be referred to as a collector plate), and a filament 336 for emitting electrons. A helium droplet beam may pass between the grid 337 and collector 338, which may be separated by a distance of ~8 mm. The grid 337 and collector 338 may both be ~2.5 cm wide, and the filament 336 may be located ~2 mm behind the grid 337. The entire assembly may be mounted inside a vacuum chamber 339 such as, for example, and without limitation, a 2.75 inch conFlat™ tee, having a window 334 that can allow an IR laser beam 342 to be counter-propagated with the droplet beam. In the exemplary embodiment, window 334 is a calcium fluoride window.

Control of the BIG detector 330 in the exemplary embodiment can be provided at least in part by a commercial ion gauge controller 350 connected to the filament 336 and grid 337. Voltage values at the grid 337 when used for the spectroscopy experiments, as described hereinbelow, are at or about +300 V, whereas the emission current at filament 336 is at or about 3.0 mA at the setpoint. The output of the collector 338 may be sent either to an oscilloscope for initial testing or to a lock-in amplifier for spectroscopy experiments.

Preliminary testing of the exemplary embodiment of BIG detector 330 was conducted with an oscilloscope connected to collector 338, which was used to evaluate operation and the detector's sensitivity and stability. When the BIG detector 330 was powered on, a DC signal (i.e., a voltage) was observed at the collector 338. This signal decreased if the droplet beam was blocked upstream of the detector. Chopping of the droplet beam produced a corresponding modulation in the voltage traces visible on the oscilloscope. Some DC contribution in the signal remained during chopping due to ionization of species such as $H_2O$ and $H_2$ in the background of the vacuum chamber 339.

Using the known impedance of the oscilloscope (1.0 MΩ), the observed voltage modulations resulted from a current of ~1.5 nA at 19 K, 50 bar nozzle conditions (a mean droplet size of ~4600 He atoms/droplet according to published scaling laws). Assuming a droplet production rate of $10^{12}$ droplets/second, and that a single $He_n+$ ion is produced from each droplet ionized, this current would correspond to the ionization and detection of ~1% of the droplets in the beam. The relative contributions to the signal from ionization of droplets as they pass between the grid 337 and collector 338, and those from ionization of helium atoms scattered from droplets evaporated upon striking the window 334, are still being evaluated. However, one of skill in the art would immediately recognize that regardless of the relative contributions, the signals from either may be usable for recording IR spectra provided that the time response of the detector is fast enough to avoid "washing out" the laser-induced modulations in the beam flux. By varying chopping frequencies, the preliminary testing revealed that the response time of the detector was sufficient to permit observation of the modulations in beam intensity at ≥100 Hz on the oscilloscope.

The root mean square noise associated with output of the collector 338 (with droplet beam chopping switched off), was measured, and a value of ~1.5 pA was obtained yielding a signal-to-noise ratio (S/N) for detection of the droplet beam of ~1000:1. Notably, the S/N ratio obtained was sensitive to the emission current applied to filament 336. For example, the S/N increased with higher emission currents, but then degraded at emission currents higher than ~3.5 mA as the filament 336 became unstable.

Satisfied that the droplet beam could be detected with an acceptable S/N ratio, and that laser-induced beam attenuation at typical chopping frequencies would not be lost, testing attention was turned to utilizing the BIG detector 330 for spectroscopy experiments. The BIG detector 330 was used to record the IR spectra of two species: $^{13}CO_2$ and $CD_4$. The former is an extremely strong IR chromophore, while the latter exhibits a more moderate absorptivity. Both are easily accessible within the tuning range (2190-2350 cm$^{-1}$) of the IR laser system used in the exemplary embodiment of system 300. After completing those experiments, the BIG detector 330 was removed, a QMS was installed, and the spectra were again recorded using the QMS as the detector. To ensure an accurate comparison, the results were obtained with only one of the two (either QMS or BIG detector 330) installed during data collection.

Shown in FIG. 6 are the normalized IR spectra 610, 620 and 630 obtained by vibrationally exciting the anti-symmetric stretching mode of $^{13}CO_2$. For these experiments, a mean droplet size of ~5900 atoms was used, and the pickup conditions were optimized for the capture of a single $^{13}CO_2$ molecule. The spectra 610, 620, 630 shown in FIG. 6 were collected using either the BIG detector 330, the QMS operating in a high-pass filter mode which integrates the signals from all ions with m/z>6 amu (620), or the QMS tuned to detect $^{13}CO_2+$ ions at 45 amu (630). In each of the spectra, the P(2), R(0), and R(2) lines of the $^{13}CO_2$ monomer are visible at 2282.55 cm-1, 2283.43 cm-1, and 2283.91 cm$^{-1}$, respectively. A band corresponding to the $(^{13}CO_2)_2$ dimer is visible at ~2284.5 cm$^{-1}$, and smaller contributions from larger $(^{13}CO_2)_n$ multimers and $^{13}CO_2$—$H_2O$ complexes formed from residual water molecules in the vacuum are also present.

The noise level, most clearly visible in an area devoid of spectral features, is shown for each spectrum in the insets 612, 622, 632 in FIG. 6. Using the standard deviation of the data shown in the insets, one can estimate the S/N ratio of the three spectra as ~300:1 for the BIG detector spectrum 610, ~1000:1 for the mass-integrated spectrum 620, and ~900:1 for the mass-selected spectrum 630. For the experiments conducted, the same parameters were employed to collect each spectrum. The only difference was the type of detector used.

In addition to the $^{13}CO_2$ spectra, the experiments also involved collection of the IR spectra of $CD_4$ in the region of the v3 CD stretching mode. These spectra 710, 720, 730 are shown in FIG. 7. For these experiments, a mean droplet size of ~3700 atoms was used, and the pickup conditions were again optimized for pickup of one $CD_4$ molecule. The spectra shown in FIG. 7 were again collected using the BIG detector 330 (spectra 710), the QMS operating in the high-pass filter mode (spectra 720), or the QMS tuned to detect CD4+ ions at 20 amu (spectra 730). Observed in the spectra was the well-known P, Q, and R branches of methane. Sharp lines located at 2251.99 cm$^{-1}$, 2255.63 cm$^{-1}$, 2259.66 cm$^{-1}$, 2263.74 cm$^{-1}$, and 266.89 cm$^{-1}$ correspond to the P(2), P(1), Q(1), R(0), and R(1) lines, respectively. Additionally, weaker signals resulting from $(CD_4)_n$ multimers and $CD_4$-$H_2O$ complexes formed from residual water molecules were present. Once again, using the standard deviation of the baseline, a S/N ratio of ~40:1 was obtained for the BIG detector 330 spectrum 712, ~50:1 for the mass integrated spectrum 720, and ~35:1 for the mass-selected spectrum 730.

Thus, as described herein, a BIG detector 330 may be used in droplet spectroscopy experiments and having a grid 337, a collector 338, and a filament 336. These components may be generally located inside a vacuum chamber 339 and may be constructed of a metal or other suitable material given their desired functions. The grid 337, for example, may be a metal mesh in a rectangular shape while the collector 338 may be a solid metal plate similar in size and shape to the grid 337. The grid 337 and collector 338 may be arranged parallel to one another with the droplet beam 321 to be measured passing between them. The filament 336 may be located behind the grid 337 and may be aligned with or arranged parallel to the beam path 332 to maximize the path length of the interaction between the droplet beam and the electrons emitted from the filament 336. The flux of the droplet beam 321 passing between the grid 337 and collector 338 may be detected as droplets that are ionized and the resulting cations contact the collector 338. Thus, photon-induced evaporation of droplets in the droplet beam 321 may be detected via the concomitant change in flux of the droplet beam 321.

The elements composing the BIG detector 330 may be manufactured from alternative materials, so long as those used for the grid 337 and collector 338 are suitable as electrodes, and have an RC time constant (resistance times capacitance) fast enough to reflect depletion of the beam by light sources 340 of up to or about 100 Hz, which is provided as an example and not a limitation. Similarly, the filament 336 may be made from a variety of materials capable of emitting electrons, and the vacuum chamber 339 may be made from any material suitable for vacuum enclosures. The BIG detector 330 may also be usable for detection of beams of clusters or droplets, such as atomic/molecular cluster beams and aerosol droplet beams.

It is clear that the example BIG detector 330 may generate usable signals for helium droplet spectroscopy experiments. The S/N obtained using this detector to acquire an IR spectrum may be, in the case of $CD_4$, comparable to that obtained using a QMS. While the QMS arrangement may provide an advantageous S/N ratio for exceptionally strong IR absorbers like $^{13}CO_2$, the S/N ratio in the IR spectrum obtained using the BIG detector 330 may be more than sufficient to record meaningful data. The BIG detector 330 may have two significant advantages. The first is that it is extremely inexpensive compared to known alternatives. Even if the ion gauge controller 350 is bought commercially, its cost may represent only a small fraction of the expense associated with the purchase of a QMS system. Another advantage is that the sensitivity of the BIG detector 330 is constant over time, on the timescale of months at least. This performance factor is in contrast to a typical QMS, in which the gain of the multiplier degrades as it ages. While the fraction of the droplet beam depleted by the laser is constant over time for both detection schemes, the absolute voltage (or current) produced in the user's data collection system may be constant for the BIG detector 330 and not constant for a typical QMS. This difference may be most often relevant when comparing spectra obtained in the same instrument over long time periods.

Thus, the BIG detector 330 may be a valid and inexpensive detection device for various spectroscopic applications, such as IR spectroscopy of doped helium droplets. It has a sufficient sensitivity, time response, and signal-to-noise ratio to permit spectroscopy experiments to be conducted on a wide variety of systems.

Embodiments of the present invention may also be directed to a method of detection in spectroscopy using a BIG detector 330 that includes a grid 337, a collector 338, and a filament 336, wherein the grid 337 may be positioned adjacent to the collector 338 to define a beam path 332 therebetween, and wherein the filament 336 may be positioned adjacent the grid 337, with the grid 337 positioned between the filament 336 and the beam path 332. Referring additionally to the flowchart in FIG. 5, the method 500 may include at Block 510 receiving an analyte beam along the beam path 332, at Block 520 emitting electrons using the filament 336; at Block 530 directing, using the grid 337, the electrons to collide with the analyte beam along the beam path 332 to produce ions, and at Block 540 detecting, using the collector 338, the ions. The filament 336 and the grid 337 may be controlled with an ion gauge controller 350 as described above.

In various embodiments of such a method, the grid 337 may be positioned substantially parallel with the collector 338, and/or the filament 336 may be substantially aligned with the beam path 332. In certain embodiments, the grid 337, collector 338 and filament 336 may be enclosed in a vacuum chamber 339 that may receive the analyte beam. The method may include, at Block 550, counter-propagating light with the analyte beam via a window 334 in the vacuum chamber 339.

Figure 8:
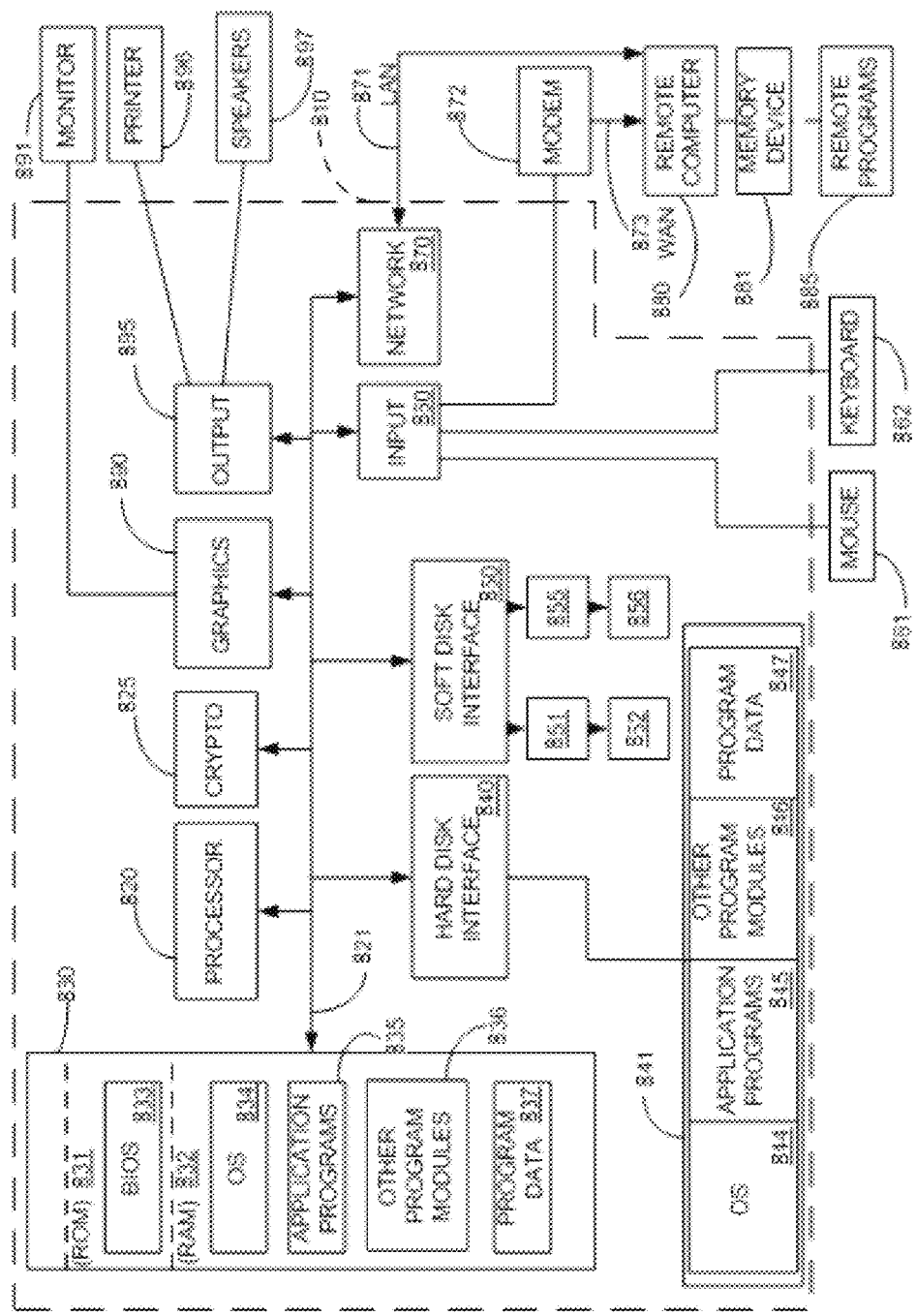
FIG. 8 is a block diagram representation of a machine in the example form of a computer system according to an embodiment of the present invention.

A skilled artisan will note that one or more of the aspects of the present invention may be performed on a computing device. The skilled artisan will also note that a computing device may be understood to be any device having a processor, memory unit, input, and output. This may include, but is not intended to be limited to, cellular phones, smart phones, tablet computers, laptop computers, desktop computers, personal digital assistants, etc. FIG. 8 illustrates a model computing device in the form of a computer 810 which is capable of performing one or more computer-implemented steps in practicing the method aspects of the present invention. Components of the computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI).

The computer 810 may also include a cryptographic unit 825. Briefly, the cryptographic unit 825 has a calculation function that may be used to verify digital signatures, calculate hashes, digitally sign hash values, and encrypt or decrypt data. The cryptographic unit 825 may also have a protected memory for storing keys and other secret data. In other embodiments, the functions of the cryptographic unit may be instantiated in software and run via the operating system.

A computer 810 typically includes a variety of computer readable media. Computer readable media can be any available media that can be accessed by a computer 810 and includes both volatile and nonvolatile media, removable and non-removable media. By way of example, and not limitation, computer readable media may include computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 8 illustrates an operating system (OS) 834, application programs 835, other program modules 836, and program data 837.

The computer 810 may also include other removable/non-removable, volatile/nonvolatile computer storage media. By way of example only, FIG. 8 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives, and their associated computer storage media discussed above and illustrated in FIG. 8, provide storage of computer readable instructions, data structures, program modules and other data for the computer 810. In FIG. 8, for example, hard disk drive 841 is illustrated as storing an OS 844, application programs 845, other program modules 846, and program data 847. Note that these components can either be the same as or different from OS 833, application programs 833, other program modules 836, and program data 837. The OS 844, application programs 845, other program modules 846, and program data 847 are given different numbers here to illustrate that, at a minimum, they may be different copies. A user may enter commands and information into the computer 810 through input devices such as a keyboard 862 and cursor control device 861, commonly referred to as a mouse, trackball or touch pad. Other input devices (not shown) may include a microphone, joystick, game pad, satellite dish, scanner, or the like. These and other input devices are often connected to the processing unit 820 through a user input interface 860 that is coupled to the system bus, but may be connected by other interface and bus structures, such as a parallel port, game port or a universal serial bus (USB). A monitor 891 or other type of display device is also connected to the system bus 821 via an interface, such as a graphics controller 890. In addition to the monitor, computers may also include other peripheral output devices such as speakers 897 and printer 896, which may be connected through an output peripheral interface 895.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810, although only a memory storage device 881 has been illustrated in FIG. 8. The logical connections depicted in FIG. 8 include a local area network (LAN) 871 and a wide area network (WAN) 873, but may also include other networks 140. Such networking environments are commonplace in offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 810, or portions thereof, may be stored in the remote memory storage device. By way of example, and not limitation, FIG. 8 illustrates remote application programs 885 as residing on memory device 881.

The communications connections 870 and 872 allow the device to communicate with other devices. The communications connections 870 and 872 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

Those skilled in the art will appreciate that the present invention contemplates the use of data structures that may store information supporting any or all of the operations involved in inventory management. The disclosure of the exemplary data structures above is not meant to be limiting in any way. Those skilled in the art will readily appreciate that data structures may include any number of additional or alternative real world data sources, and may be configured in any way while still accomplishing the many goals, features and advantages according to the present invention.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. Thus, the scope of the invention should be determined by the appended claims and their legal equivalents, and not by the examples given.

I claim:

1. A beam ionization gauge (BIG) detector for use in spectroscopy and configured to receive an analyte beam along a beam path, the BIG detector comprising a vacuum chamber configured to receive the analyte beam, said vacuum chamber comprising a window configured to receive light from a source to be counter-propagated with the analyte beam and enclosing:
   a filament configured to emit electrons;
   a grid positioned substantially adjacent to the filament and configured to direct the electrons to collide with the analyte beam along the beam path to produce ions; and
   a collector positioned substantially adjacent to the grid to define the beam path there between and configured to detect the ions produced by the grid directing electrons to collide with the analyte beam along the beam path.

2. The BIG detector according to claim 1 wherein the grid is positioned substantially parallel with the collector.

3. The BIG detector according to claim 1 wherein the filament is substantially aligned with the beam path.

4. The BIG detector according to claim 1 wherein the analyte beam comprises a solvent and a dopant.

5. The BIG detector according to claim 4 wherein the solvent comprises at least one of droplets and clusters.

6. The BIG detector according to claim 1 further comprising an ion gauge controller coupled to the filament and the grid.

7. A spectroscopy system comprising:
   a beam source configured to produce a solvent beam;
   a pickup region configured to receive the solvent beam and add dopants thereto to define an analyte beam;
   a beam ionization gauge (BIG) according to claim 1;
   an ion gauge controller coupled to the filament and the grid;
   a source configured to generate light to interact with the analyte beam; and
   an analyzer configured to receive an output from the collector.

8. The spectroscopy system according to claim 7 wherein the beam ionization gauge's grid is positioned substantially parallel with the collector.

9. The spectroscopy system according to claim 7 wherein the beam ionization gauge's filament is aligned with the beam path.

10. The spectroscopy system according to claim 7 wherein the beam source is configured to produce the solvent beam including at least one of droplets and clusters.

11. The spectroscopy system according to claim 7 wherein wherein the source comprises a laser configured to generate a laser beam through the window to be counter-propagated with the analyte beam.

12. A method of detection in spectroscopy using a beam ionization gauge (BIG) detector that includes a vacuum chamber configured to receive an analyte beam, said vacuum chamber comprising a window configured to receive light from a source to be counter-propagated with the analyte beam and enclosing a grid, a collector, and a filament, wherein the grid is positioned adjacent to the collector to define a beam path there between, and wherein the filament is positioned adjacent the grid, with the grid positioned between the filament and the beam path, the method comprising:
   receiving an analyte beam along the beam path;
   emitting, using the filament, electrons;
   directing, using the grid, the electrons to collide with the analyte beam along the beam path to produce ions; and
   detecting, using the collector, the ions.

13. The method according to claim 12 wherein the grid is positioned substantially parallel with the collector.

14. The method according to claim 12 wherein the filament is substantially aligned with the beam path.

15. The method according to claim 12 further comprising: enclosing the grid, collector and filament in a vacuum chamber; and receiving the analyte beam using the vacuum chamber.

16. The method according to claim 15 further comprising counter-propagating light with the analyte beam via a window in the vacuum chamber.

17. The method according to claim 12 wherein the analyte beam comprises at least one of droplets and clusters.

18. The method according to claim 12 further comprising controlling the filament and the grid with an ion gauge controller.

* * * * *